United States Patent [19]

Pike

[11] 3,977,401

[45] Aug. 31, 1976

[54] INJECTION APPARATUS

[76] Inventor: William Floyd Pike, 609 W. Iron, Hobbs, N. Mex. 88240

[22] Filed: Mar. 25, 1975

[21] Appl. No.: 559,961

[52] U.S. Cl. .................. 128/218 D; 128/218 R; 128/221
[51] Int. Cl.² .................................. A61M 5/00
[58] Field of Search .......... 128/218, 216, 215, 225, 128/173, 220, 221; 222/389, 394

[56] References Cited
UNITED STATES PATENTS

| 3,066,670 | 12/1962 | Stauffer | 128/218 F |
|---|---|---|---|
| 3,115,133 | 12/1963 | Morando | 128/173 H |
| 3,527,212 | 9/1970 | Clark | 128/215 X |
| 3,587,575 | 6/1971 | Lichtenstein | 128/215 |
| 3,605,744 | 9/1971 | Dwyer | 128/218 F |
| 3,788,315 | 1/1974 | Laurens | 128/173 H |

*Primary Examiner*—John D. Yasko
*Attorney, Agent, or Firm*—Henry Heyman

[57] ABSTRACT

An apparatus for parenteral administration of medications is disclosed herein. The apparatus, in a preferred embodiment, is completely self-contained, i.e., all components normally required for intramuscular injection including antiseptic and antiseptic applicator for disinfection of the injection site, hypodermic needle, unit dose of injectable medication and means of automatically effecting injection of said unit dose are contained within the subject invention. An injection method is also described herein.

4 Claims, 11 Drawing Figures

INJECTION APPARATUS

BACKGROUND OF THE INVENTION

The present invention relates generally to an apparatus and method to facilitate intramuscular injection of medications in essentially an automatic manner.

Heretofore, intramuscular injections have been accomplished in a rather laborious fashion and were accompanied by inherent limitations and disadvantages from the point of view of the injection recipient as well as that of those administering such injections. Two general methods or cases will be cited to illustrate this point.

In the first method, a sterile needle in a protective sheath is affixed to a sterile glass or plastic syringe, followed by insertion of the needle into a recently disinfected vial or ampule from which the desired medication in specific quantity is drawn in order to ready the syringe for injection. The skin at the injection site is disinfected and ordinarily allowed to dry. The needle is inserted into the tissues at the desired site, ideally without lateral motion, the plunger of the syringe depressed by digital pressure to expel its contents into the tissues following which the needle is withdrawn, again ideally without lateral motion. Although the actual sequence of events may vary depending upon the training and preference of those administering intramuscular injections, the basic method is as described.

In the second method a unit dose cartridge with sterile needle in a protective sheath is positioned in a hinged metal frame, screwed into position, the upper portion of the metal frame swung into position over the vial and locked so that the metal plunger lies above the vial, following which the protective sheath covering the needle is removed. Insertion of the needle into a disinfected injection site is accomplished, ideally without lateral motion, the metal plunger depressed to expel contents of the vial into the tissues, and the needle withdrawn, again, ideally, without lateral motion.

In the first method both the skin and medication container must be disinfected by pads, swabs, sponges or other absorbent materials impregnated with a standard antiseptic or cleansing solution such as an alcohol or Betadine. This may be accomplished by manual impregnation of dry sterile absorbent material or by using prepared impregnated absorbent material individually packed in metal foil tear-open packets. In any event, attention must be given to acquisition and administration of a separate item before an injection may be made. This constitutes a minor inconvenience at best.

Secondly, aseptic technique must be rigidly adhered to in manipulation of the syringe and needle. The needle in its sheath must be carefully affixed to the syringe in a separate manual operation. The needle sheath must be carefully removed, again as a separate portion of the overall procedure. An ampule must be aseptically opened, the needle inserted in an aseptic manner, medication drawn into the syringe in specific quantity — each as a separate and time-consuming operation prior to injection. In the case of multiple use vials, room air must be drawn into the syringe, the air expelled into the vial, the medication drawn up, and the needle withdrawn from the vial through the hole made in its septum — again each as time-consuming and inconvenient separate procedures and, as noted, involving acquisition of separate items, viz. ordinarily a disposable needle in its container, a disposable syringe in its container, and medication in ampule or vial form. Regardless of the nature of the container, i.e., either ampule or vial, there is an element of risk involving contamination of the needle or of the medication in its container by microorganisms in the immediate environment or by those which may be present in the air injected in the pressure equalization operation necessary before medication may be withdrawn from a vial.

In the second method a number of the previously noted disadvantages remain as well as development of other objections to be noted below. Again the skin must be disinfected necessitating acquisition and administration of a separate antiseptic-impregnated material. The metal frame of the syringe must be opened for insertion of the cartridge, the latter consisting of a unit dose of medication with an attached sterile needle in a protective sheath. The cartridge must then be rotated clockwise until the needle ferrule is engaged, fixed in a locked position, the open metal frame swung into position and locked, the plunger attached to the threaded end of the piston, the needle sheath removed, the needle inserted into tissue at the injection site, the plunger depressed, the needle removed, the metal frame opened, following which the cartridge is rotated counterclockwise, removed from the metal frame, and discarded — each as separate procedures.

As will be noted from consideration of the foregoing, both methods are inconvenient, time-consuming, agonizingly slow in emergency procedures, and are accompanied by what will subsequently be seen as largely avoidable risk of infection or sterile abcess formation.

Discussion of the limitations and disadvantages of current intramuscular injection techniques would not be complete without noting the adverse psychological effect on the patient of an exposed hypodermic needle or of a contraption of metal, glass, and exposed needle which bears a strong resemblance to syringes used to inject large animals in veterinary medicine.

The present invention abrogates the foregoing disadvantages by providing an uncomplicated and self-contained apparatus which affords a means of essentially automatic and uniform intramuscular injections, regardless of widely differing abilities to administer such injections.

SUMMARY OF THE INVENTION

An object of the present invention is to provide a self-contained and disposable apparatus for, in particular, intramuscular injection of medications, said apparatus containing antiseptic and antiseptic applicator, hypodermic needle of appropriate gauge and length, medication in unit dose form, and propulsion means for needle insertion and medication injection.

Another object of the present invention is to provide an apparatus which has unit dose capability from less than 1 cubic centimeter to 10 or more cubic centimeters capacity.

Yet another object of the present invention is to provide an injection apparatus which ensures uniform administration of intramuscular medications and which minimizes tissue trauma, regardless of training and experience of the user.

Still another object of the present invention is to provide an injection apparatus of less menacing appearance by concealing contents (including hypodermic needle) from the vision of the patient, relatives and casual observers.

A further object of the present invention is to provide an apparatus which effects essentially automatic intramuscular injections by nurses, physicians, veterinarians, diabetics, and others who may lawfully be entitled to use such devices.

Another object of the present invention is to ensure single or one-time use of the apparatus so that unauthorized and repeated use is prevented. Inventory of controlled substances will be more easily facilitated, as will reduction of pilferage of narcotics and other controlled substances. The incidence of serum hepatitis may also be reduced to some extent by proper use of the subject invention.

Still another object of the present invention is to provide a means whereby a fluid (gas or liquid, but preferably gas), contained within subject invention or attached thereto, exerts sufficient pressure to force a hypodermic needle into tissues at an injection site to a desired depth and which then forces a particular dose of medication from a container into the tissues at a specified rate.

Yet another object of the present invention is to provide an injection method having the foregoing features.

Another object of the present invention is to employ a modification thereof to effect automatic reconstitution of dehydrated or lyophilized medications for intramuscular injection.

Still another object of the present invention is to employ a modification thereof to allow aspiration, a feature deemed necessary by many but, in practice, performed by few.

A further object of the present invention is to provide a modification thereof to be used as a possible nonlethal means of controlling rioting or looting crowds or of apprehending fleeing suspects without resort to lethal weapons by, e.g., formic acid injection by projectiles.

Another object of the present invention is to provide a means whereby unskilled individuals may inject themselves or another individual in life-threatening situations such as exposure to nerve gases or other toxic chemical agents or in acute cardiac disorders, said administration dictated by previous agreement with a physician.

These objectives and other objects and features to become apparent hereinafter are attained by an apparatus or modification of an apparatus constructed in accordance with the present invention.

Briefly, a tear tab is removed from one end of the apparatus, thereby removing a foil covering and permitting exposure of the antiseptic applicator which is attached to the apparatus. The apparatus is then used as a supportive handle for the applicator, the applicator being rubbed over the injection site while still attached to the apparatus. The applicator is then removed so as to expose that portion of the apparatus through which the lower needle will pass. Contents of the apparatus are not visible to the patient or an observer, however, thereby eliminating much apprehension. The apparatus is placed with the aperture against the skin, thereby ensuring continued sterility of the contents of the apparatus.

A preferred embodiment of the invention also includes control means of activating a cartridge containing gas unde pressure, which then forces an inspected medication-containing cartridge of specialized construction against one end of a double-ended needle assembly, said end penetrating a septum of the cartridge thereby affording a channel through which medication will shortly pass from cartridge to tissues at the injection site. The now-coupled needle assembly and medication cartridge remove shear tabs due to gaseous pressure which continues to propel the assembly and retained shear tabs through the barrel of the apparatus. The other end of the double-ended needle penetrates the musculature to an extent dictated by the length of the needle. Only when the needle is seated in the musculature is the cartridge plunger exposed to increased gas pressure, thereby forcing the plunger to expel the medication into the tissues. The process of penetration and injection are nearly instantaneous, although by altering the design slightly, the medication may be injected at any predetermined rate. The needle is then withdrawn from the tissues by withdrawing the apparatus without lateral motion.

The cartridge is inspected to ensure delivery of the medication in the desired site and the assembly is then discarded. Means of inspection of the cartridge before and after injection will become apparent in the detailed description to follow.

DETAILED DESCRIPTION

Figure 1:
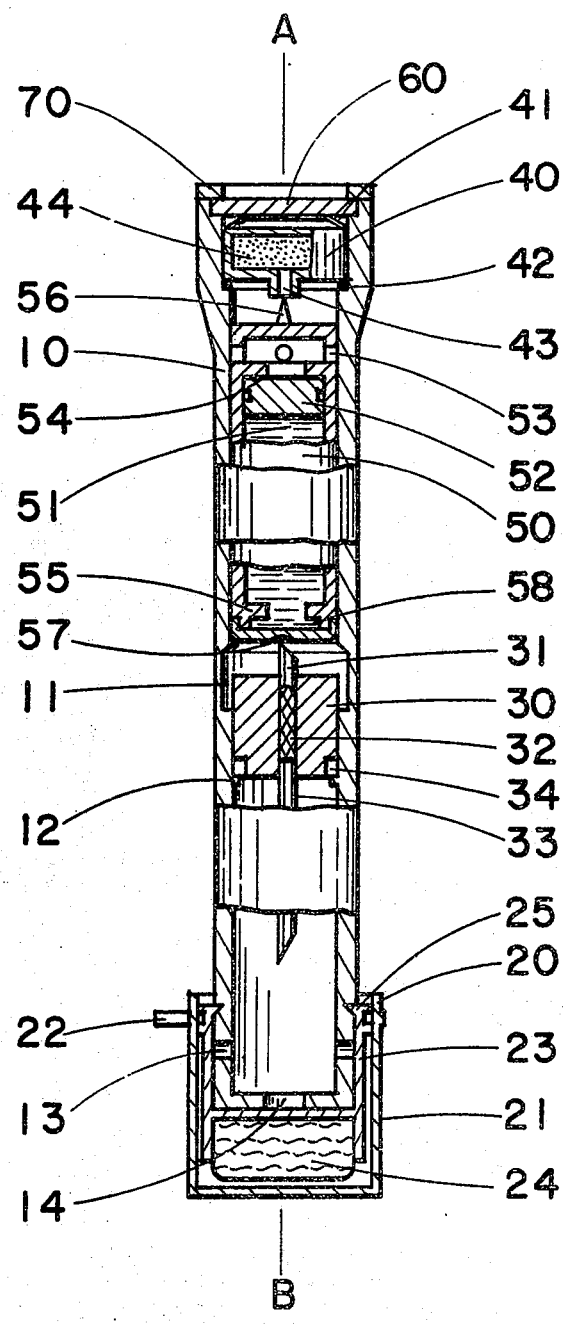
FIG. 1 illustrates an enlarged side elevational view, in cross section, of the components of the apparatus constituting the present invention.
Figures 2A, 2B, 2C, 2D, 2E, 2F, 2G, 2H, 2I:
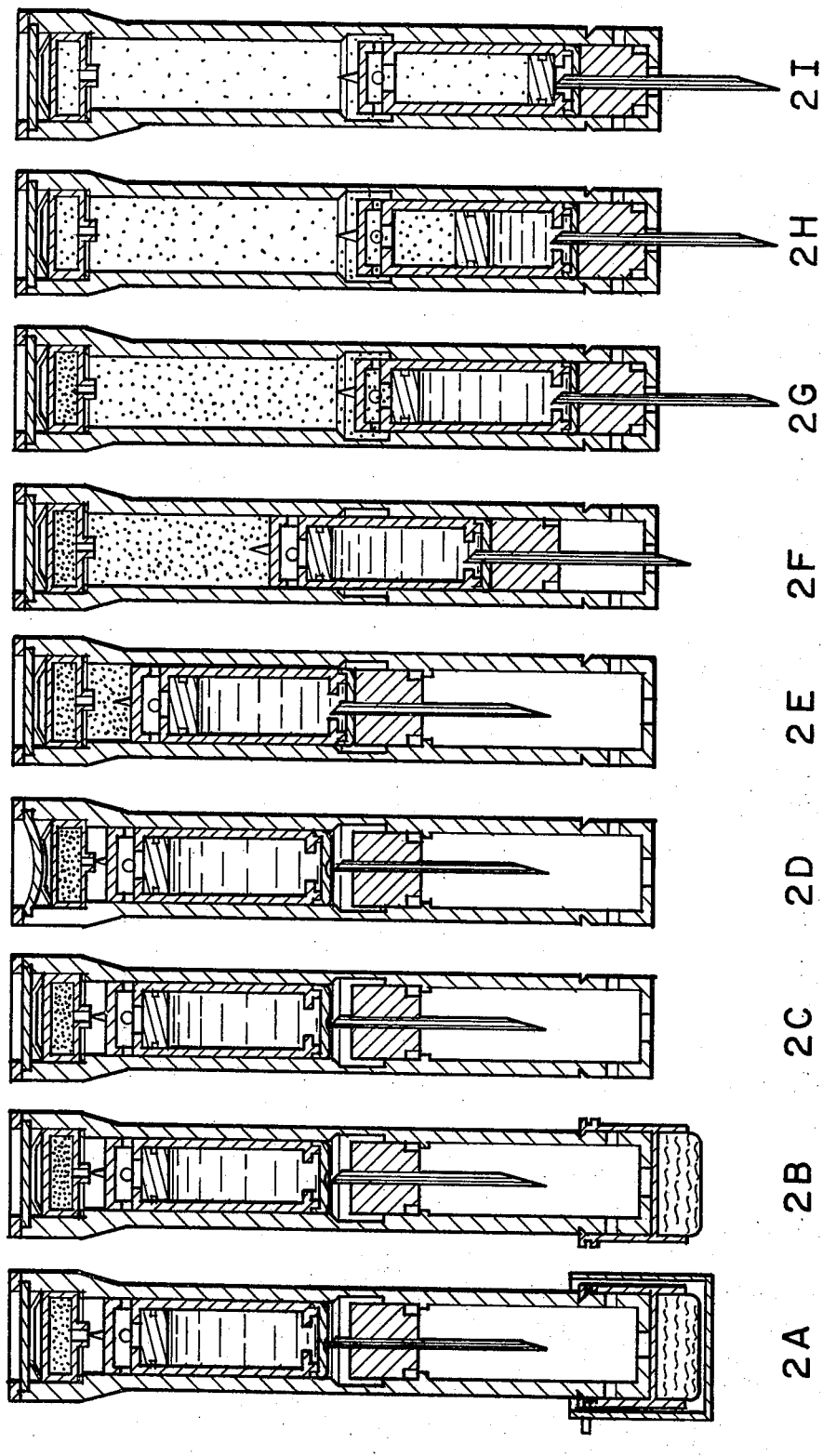
FIG. 2 A through FIG. 2 I illustrate a series of side elevational views in cross section of the present invention to approximate scale for 2 cubic centimeters of medication and depicts the sequence from the intact, unopened apparatus in FIG. 2 A through completion of medication injection in FIG. 2 I.

Turning to the drawings, wherein like features or components are designated by like reference numerals throughout the FIGURES, attention is directed to FIG. 1 which illustrates in enlarged cross sectional view the components and features of the present invention and which must be referred to in understanding operational sequence views as depicted in FIG. 2 A through FIG. 2 I.

Figure 3:
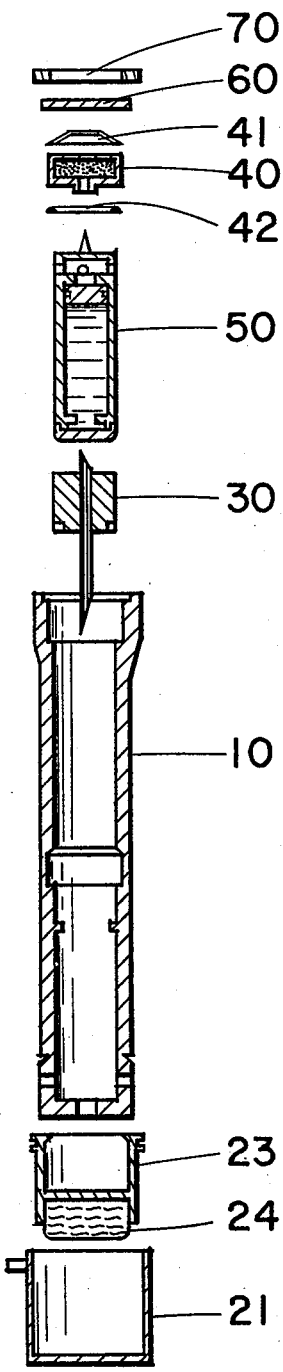
FIG. 3 illustrates a side elevational view in cross section of the individual components or component assemblies depicting thereby, and as discussed subsequently, a suggested means of assembly of the apparatus constituting the present invention.

As will be seen from reference to FIG. 1 and FIG. 3, the apparatus consists generally of an assembly tube 10 within which, or attached thereto, are separable components now to be described in part. Viewed along the line A — B attention is directed to activation septum 60, recessed and sealed in place by activation septum seal 70. Plastic spring 41 is designed to distribute mechanical pressure evenly circumferentially about propellent assembly 40 when activation septum 60 is depressed, as will be seen subsequently. Propellent assembly 40 containing gas 44 under pressure rests upon flexible annular support 42 which in turn is supported by a shoulder of assembly tube 10.

Proceeding downward along the line A - B, within assembly tube 10 is medication cartridge assembly 50 which is, as will be seen in subsequent FIGURES and discussion, of specialized design. Propellent seal perforator 56, attached to cartridge assembly 50, is in tangential contact with propellent seal and exhaust port 43. Medication assembly 50 is supported within assembly tube 10 by contact of septum 57 with upper needle 31. needle assembly 30, in turn, is supported within assembly tube 10 by means of shear tabs 12. As will become apparent in subsequent discussion concerning FIG. 2 A through FIG. 2 I, it is desirable that the internal surface of assembly tube 10 and the external surfaces of needle assembly 30 and medication cartridge assembly 50 possess minimal friction coefficients.

The antiseptic applicator assembly, generally indicated by the numeral 20, is attached to the base of assembly tube 10 by means of applicator support retainer 25 which engages a circumferential depression of assembly tube 10. Applicator support retainer 25 further serves to effect a seal between assembly tube 10 and the external environment thereby assuring maintenance of sterile conditions within assembly tube 10.

Surrounding applicator support 23 and antiseptic applicator 24 is a covering 21, preferably of metallic foil, which is affixed to applicator support retainer 25 by means of tear tab 22 such that an airtight seal is effected to prevent evaporation of the antiseptic in antiseptic applicator 24.

Turning now to FIG. 2 A through FIG. 2 I, the sequence of events involved in operation of the invention will be discussed. FIG. 2 A depicts the intact invention previously described with features heretofore not mentioned in discussion of FIG. 1 to be subsequently noted and explained in detail.

FIG. 2 B illustrates the appearance of subject invention following removal of foil covering 21 by means of tear tab 22. Note that applicator support 23 and antiseptic applicator 24 remain attached to assembly tube 10 by means of applicator support retainer 25, thereby assuring maintenance of sterility within assembly tube 10. Assembly tube 10 is then used as a supportive handle to facilitate applicatin of antiseptic by means or rotating assembly tube 10 so that antiseptic applicator 24 is in intimate contact with the intended injection site.

In FIG. 2 C antiseptic applicator assembly 20 has been manually removed by pulling applicator support 23 along the line A - B of FIG. 1, thereby dislodging applicator support retainer 25 from the circumferential depression in assembly tube 10. The assembly tube base 15 is in contact with the skin at the injection site.

In FIG. 2 D, activation septum 60 is depressed by digital pressure forcing plastic spring 41 to apply circumferential pressure on propellent assembly 40. Due to said pressure propellent assembly 40 depresses flexible annular support 42, thereby allowing propellent seal 43 to be penetrated by propellent seal perforator 56. Perforation of propellent seal 43 affords a pathway for compressed gas 44 to escape through propellent seal and exhaust port 43.

Attention is now directed to FIG. 2 E. Release of gas 44 to the interior of assembly tube 10 is restricted by the presence therein of medication cartridge assembly 50. The sudden increase in gas pressure above medication assembly 50 forces the latter to begin moving downward within assembly tube 10 along the line A - B of FIG. 1. It will be noted in FIG. 2 E that septum 57 of medication cartridge assembly 50 has been penetrated by upper needle 31 of needle assembly 30, thereby affording a pathway for medication 51 to fill the needle of needle assembly 30 by capillarity and, at the appropriate time, to permit medication injection.

In FIG. 2 F shear tabs 12 have been forcibly removed by pressurized descent of the now-coupled needle assembly 30 and medication cartridge assembly 50, said separated shear tabs 12 being retained by shear tab retention depressions 34. Lower needle 33 is at this time passing through lower needle exit port 14 and initiating penetration of the tissues at the injection site. Also with respect to FIG. 2 F, it should be noted that descent of coupled needle assembly 30 and medication cartridge assembly 50 forces air through air exhaust perforations 13 thus permitting escape of air which would otherwise be entrapped and interfere with continued descent of needle assembly 30 and medication cartridge assembly 50 and which would therefore prevent successful operation of the subject invention. It must also be noted that expended propellent gas 44 is restricted to the volume within assembly tube 10 which lies between the bottom of propellent assembly 40 and the top of medication cartridge assembly 50.

Referring now to FIG. 2 G, it will be noted that coupled needle assembly 30 and medication cartridge assembly 50 have undergone maximum displacement with the leading edge of needle assembly 30 firmly lodged against assembly tube base 15. Lower needle 33 has achieved maximum penetration of the tissues at this time.

Gas 44 is no longer restricted in the manner previously described but may now pass into and through fluid channel 11 and thence through medication cartridge perforations 53 to the upper chamber of medication assembly 50 thereby exposing the upper surface of cartridge piston 52 to increased pressure from gas 44. In FIG. 2 G it should be noted that piston 52 has not yet been depressed and that the periphery of its upper surface is in contact with cartridge upper stop 54. Therefore the volume of injectable medication 51 in medication cartridge assembly 50 is defined by the lower surface of cartridge piston 52 and the upper surface of cartridge lower stop 55. In FIG. 2 A through 2 I the drawings are approximately to scale and therefore the volume of injectable medication 51 may be shown to be approximately 2 cubic centimeters.

FIG. 2 may be considered essentially a mid-position view involving injection of medication 51. In this FIGURE it will be seen that gas 44 has exerted sufficient pressure upon the upper surface of cartridge piston 52 so as to force medication 51 through the double-ended needle of needle assembly 30 and into the tissues of the injection site.

In FIG. 2 I injection of medication 51 has been completed since the lower surface of cartridge piston 52 has been engaged and stopped by contact with the upper surface of cartridge lower stop 55, thereby preventing upper needle 31 from contacting or penetrating the lower surface of cartridge piston 52 so as to preclude the possibility of gas 44 entering the needle of needle assembly 30. It must also be pointed out that although a minute amount of medication 51 remains in residual medication chamber 58, as previously noted the desired volume of medication 51 has been injected into the tissues.

The lower needle 33 is then withdrawn from the tissues without lateral motion by pulling directly upward on assembly tube 10. After inspection to verify injection of medication 51, the apparatus and antiseptic application assembly are discarded.

Attention is now directed to FIG. 3 which depicts a suggested means of assembly of the components comprising the present invention.

It is suggested that all components be pre-sterilized by exposure to a gas toxic to microorganisms such as ethylene oxide and then assembled aseptically, preferably by machine, with additional sterilization stages where necessary.

One logical means of assembly is as follows: (It will be necessary to refer occasionally to FIG. 1.)

1. Antiseptic applicator support 23 and antiseptic applicator 24 saturated with antiseptic are affixed to assembly tube 10 by means of applicator support retainer 25 which engages the circumferential depression in assembly tube 10 thereby effecting closure and seal of the lower portion of assembly tube 10.

2. Covering 21 is then placed in position over applicator support 23, thereby enclosing applicator support 23 and antiseptic applicator 24.

3. Tear tab 22 is drawn tightly over covering 21 thereby engaging the circumferential groove in applicator support 23 and effecting an air-tight seal.

4. Sterile needle assembly 30 is lowered into sterile assembly tube 10 and is supported in position on shear tabs 12.

5. Sterile medication cartridge assembly 50 is then lowered into assembly tube 10 and is supported by contact between septum 57 and upper needle 31.

6. The remainder of the assembly process may be performed under clean conditions, but aseptic technique should not be required. Flexible annular support 42 is placed in assembly tube 10 and is supported by a circumferential shoulder of assembly tube 10.

7. Propellent assembly 40 is placed in assembly tube 10, resting upon flexible annular support 42.

8. Thereafter plastic spring 41 is placed upon the upper periphery of propellent assembly 40.

9. Activation septum 60 is then placed in position over plastic spring 41.

10. Final stage of assembly involves addition of activation septum seal 70 to assembly tube 10. Coupling may be effected by traditional means such as threaded coupling, pin or rivet-type coupling, quick connectors, or by use of powerful adhesives.

It is obvious, however, that one or more of the preceding assembly steps may be combined in order to reduce expense of assembly and expedite production of subject invention.

Having discussed the operation and suggested means of assembly, attention is now directed to features of subject invention not yet discussed in detail.

As previously noted, the effect of viewing an exposed hypodermic needle is psychologically traumatic for most patients and nearly overwhelming for some. Many animals other than man also associate the appearance of a hypodermic needle with impending pain. The usual result is voluntary of involuntary muscular contraction, particularly at the intended injection site. Such contraction makes needle insertion more difficult and leads to needless additional tissue trauma. Subject invention obviates this objection and reaction, however, since the needle is hidden from the patient's view. In addition, since needle penetration is standardized and the actual injection process is almost instantaneous using the present invention, uniformity and brevity of intramuscular injection is assured. Therefore, regardless of training, background, or experience any individual will be capable of administering what patients refer to as "good shots".

Concealment of contents of subject invention may be effected inexpensively by spray-painting the exterior surface of assembly tube 10 in attractive colors to render it translucent or opaque prior to sterilization and assembly. However, since it is vitally important that the invention in general and sterile medication cartridge assembly 50 be inspected by the user prior and subsequent to injection, it is suggested that a narrow portion extending the length of assembly tube 10 be masked prior to spray-painting. The masking may be left in place until use thereby protecting medication 51 from exposure to potentially detrimental incident light. Indeed, the masking itself may be appropriately labeled so that when the masking is removed immediately prior to injection the user is assured that the medication to be administered is, in fact, that which was prescribed and in correct dosage.

Color coding capability may further aid this goal. As an additional precaution, however, activation septum 60 and/or activation septum seal 70 may be labeled and/or color coded and inspected prior to application of digital pressure to activation septum 60. (It is a well known fact that many patients have mistakenly received incorrect parenteral medication, occasionally with fatal results.)

It must be emphasized that subject invention without modification thereof does not provide aspiration capability deemed necessary by many but, in practice, observed by few. Most injection accidents leading to anaphylactic and related reactions are due to tissue damage at the injection site as a result of inept injection technique. Such accidents are therefore largely preventable and also relatively rare. Proper use of subject invention and basic knowledge of anatomy should lead to even fewer injection accidents. However, to placate those who insist on an aspiration feature, a separate application will be filed disclosing a modification of the present invention which incorporates the aspiration feature.

Lastly, current techniques for reconstitution of powdered or lyophilized parenteral medications are, although essential for obvious reasons, relatively cumbersome and time-consuming as well as being associated with a recognized risk of contamination by microorganisms. Therefore a separate application will be filed which discloses a modification of subject invention and which rehydrates powdered or lyophilized medications essentially automatically prior to their injection.

I claim:

1. A disposable automatically operated hypodermic syringe for injecting medication into a patient comprising:
   a. a unitary elongated tubular housing having a first end and a second end, said housing first end having a cylindrical shaped relief in the inner wall thereof extending from the end of the housing to a shoulder formed by the unrelieved adjacent portion of the housing, and the second end of the tubular housing being the injecting end and being provided with a transverse end wall having a centrally located axial aperture therethrough, air escape port means penetrating the side wall of the housing proximate the said second end;
   b. a hypodermic needle supporting piston slidably supported in an intermediate portion of said housing, a hypodermic needle axially supported in and hermetically affixed to the needle supporting piston, and having a sharpened end protruding from a first face of the needle supporting piston in the direction of the first end of the housing, and an elongated stem with sharpened end projecting from a second face of the needle supporting piston in the direction of the second end of the housing, at least one shearable tab affixed to the inner wall of the housing to abut against the second face of the needle supporting piston to maintain the elongated stem of the hypodermic needle retracted within said tubular housing until said syringe is operated, c. an elongated hollow medication cartridge slidably supported in said tubular housing adjacent to and upstream of the needle supporting piston in the direction of the first end of the tubular housing, said medication cartridge having a puncturable transverse end closure in proximity to the needle sharpened end protruding from the first face of the needle supporting piston and a transverse end wall with an aperture therethrough affixed to its other end, a medication cartridge piston slidably supported inside the medication cartridge and positioned adjacent the said other end of the medication cartridge, said medication cartridge being adapted to be filled throughout its remaining interior space with fluid medication;

d. an internal annular valve recess in the interior wall of said housing at a position distant from the internal surface of the transverse wall at the second end of the housing equal approximately to the combined axial lengths of the needle supporting piston and the medication cartridge, e. a compressed gas cartridge slidably supported in hermetically sealed relation in the housing first end relief, an annular axially compressable spring member supported in said relief between the compressed gas cartridge and the shoulder of the relief, said compressed gas cartridge having a puncturable end closure facing the interior of the housing, f. a cylindrical slidable valve member having a transverse substantially rigid end closure facing the compressed gas cartridge, a pointed penetrator affixed to the end closure with the point proximate the compressed gas cartridge puncturable end closure, at least one port aperture penetrating the slidable valve member cylindrical side wall, the open end of the slidable valve member abutting the medication cartridge, g. a disc shaped depressible closure member affixed to the first end of the housing proximate the adjacent wall of the compressed gas cartridge and adapted when depressed to force the cartridge against the pointed penetrator to release the compressed gas, whereby gas pressure against the slidable valve member urges the medication cartridge into rupturable contact and communication with the hypodermic needle, and whereby said gas pressure forces the needle supporting piston to shear the at least one retaining tab, and to move the needle supporting piston, the needle, the medication cartridge and the slidable valve member together toward the second end of the housing at which position the stem of the hypodermic needle has been inserted into the patient and the slidable valve member is in the internal annular recess in the housing, whereby gas pressure passes into the interior of the slidable valve member and into the medication cartridge to force the medication piston along the length of the medication cartridge thereby injecting the medication into the patient.

2. The disposable automatically operated hypodermic syringe of claim 2 in which a detachable cylindrical end closure, having an interior transverse septurm, is telescopable over the housing second end with the septum abutting the housing end wall thereby hygienically sealing said housing, and an antiseptic bearing pad is affixed in the open end of the cylindrical end closure with a portion of the pad extending outwardly therefrom.

3. The disposable automatically operated hypodermic syringe of claim 2 in which the detachable cylindrical end closure has a deformable inwardly directed protrusion, and the housing is provided with a recess for engaging said protrusion thereby assuring retention in place of the end closure to maintain the internal sterility of the syringe.

4. The disposable automatically operated hypodermic syringe of claim 3 in which a cup shaped foil covering surrounds the detachable cylindrical end closure and is detachably affixed to the exterior wall of the housing.

* * * * *